US008893970B2

(12) United States Patent
Keefe et al.

(10) Patent No.: US 8,893,970 B2
(45) Date of Patent: Nov. 25, 2014

(54) METHOD AND APPARATUS FOR LABELING A MEDICINAL SUBSTANCE

(71) Applicants: Gary Keefe, Brecksville, OH (US); Lawrence Srnka, Northfield Center, OH (US); Michael Kolberg, Hinckley, OH (US); Timothy Jablonski, Lakewood, OH (US)

(72) Inventors: Gary Keefe, Brecksville, OH (US); Lawrence Srnka, Northfield Center, OH (US); Michael Kolberg, Hinckley, OH (US); Timothy Jablonski, Lakewood, OH (US)

(73) Assignee: Codonics, Inc., Middleburg Heights, OH (US)

( * ) Notice: Subject to any disclaimer, the term of this patent is extended or adjusted under 35 U.S.C. 154(b) by 59 days.

(21) Appl. No.: 13/778,913

(22) Filed: Feb. 27, 2013

(65) Prior Publication Data

US 2013/0221087 A1    Aug. 29, 2013

Related U.S. Application Data

(60) Provisional application No. 61/603,533, filed on Feb. 27, 2012.

(51) Int. Cl.
*G06F 19/00* (2011.01)
*G06Q 10/00* (2012.01)
*G06Q 50/22* (2012.01)

(52) U.S. Cl.
CPC ............... *G06Q 50/22* (2013.01); *G06Q 10/00* (2013.01)
USPC .......................................... 235/385; 235/375

(58) Field of Classification Search
USPC .................................................. 235/375, 385
See application file for complete search history.

(56) References Cited

U.S. PATENT DOCUMENTS

2006/0144919 A1*   7/2006   Tong ............................. 235/375
2008/0314978 A1*   12/2008   Fedorko et al. ............... 235/385

* cited by examiner

*Primary Examiner* — Jamara Franklin
(74) *Attorney, Agent, or Firm* — Pearne & Gordon LLP (57) ABSTRACT

Provided is a method for reading a code from a container of a medicinal substance and printing a label for the container. The method includes reading a machine readable code associated with a container for storing a medicinal drug. The machine readable code includes an identification information of the medicinal drug. The method also for determining a useful life of the medicinal drug based on a time at which the container for storing the medicinal drug was initially accessed and encoding a label content including the useful life of the medicinal drug. The method also includes printing a label including the label content including the useful life of the medicinal drug.

21 Claims, 9 Drawing Sheets

METHOD AND APPARATUS FOR LABELING A MEDICINAL SUBSTANCE

BACKGROUND OF THE INVENTION

1. Field of the Invention

This application relates generally to scanning machine readable codes, determining an expiration of medicinal substance contained in a storage device due to an initial access of the storage device, and printing a label to indicate the expiration due the initial access. The application also relates to an apparatus for scanning and printing labels in medical applications where medicinal substances have variable expiration times due to different environments.

2. Description of Related Art

Medicinal substances may have different expiration times depending on the different environments they encounter. For example, the life expectancy of medicinal substances may drastically shorten after they are initially accessed in a container (e.g. vial) due to oxygen entering the vial and degrading the medicinal substance. For example, a medicinal substance with a shelf life of 6 months in an unopened container may have a shorter shelf life of 12 hours once the container storing the medicinal substance has been breached. Additionally, medicinal substances may have different life expectancies in different containers. A medicinal substance in one container may have a life expectancy of 12 hours. However, the life expectancy of that same medicinal substance in a different container such as a syringe may only be 6 hours.

Traditionally, medicinal substances arriving at a hospital, pharmacy, or other location where the medicinal substance is to be accessed arrive with a label bearing content provided by the supplier or manufacturer. In the event a label is to be administered to a container of the medicinal substance, such labels can be manually created by handwriting the desired label content onto label stock. For instance, technicians preparing a dose of the medicinal substance extract the appropriate amount of the medicinal substance from a vial into a syringe. At a time when the syringe was being prepared, the technician would retrieve the adhesive-backed label stock from a bin and write a notation on the label indicative of the medicinal substance to be administered. Once the syringe was prepared, the hand-written label would be applied to the syringe to notify those who may encounter the syringe of its contents.

Such conventional labeling systems suffer from many drawbacks, and have limited reliability due primarily to human error. Sloppy handwriting can make the label difficult to read, or altogether illegible. Each technician who prepares such a label may also do so in a different manner, or attribute different meanings to the content of a label than another technician. In such situations, the label content is left open to interpretation, and often lacks information essential for proper documentation and record keeping purposes.

Additionally, it is difficult for a technician to keep track of and/or calculate life expectancies of medicinal substances when the life expectancies of the medication vary between the source vial containing the medicinal substance and a syringe or other delivery means for administering the medicinal substance. Thus, medicinal substances that have un-accessed life expectancy in a source container, an accessed life expectancy in a source container, and a delivery life expectancy in a delivery device all complicate the determination of expiration for medicinal substances.

BRIEF SUMMARY

Accordingly, there is a need in the art for a method and apparatus for generating a machine-printed label to provide information indicating a useful life of the medicinal substance.

According to one aspect, the subject application involves a terminal for labeling a medicinal substance with a scanner that scans a first machine-readable code from a source container that stores the medicinal substance for delivery to a patient. Labeling a medical substance also includes a processor component. The processor component includes a substance identification component to determine an identity of the medicinal substance stored in the source container based on the scan of the first machine-readable code. The processor component also includes a usage component to establish when the source container was initially accessed and a labeler component that generates a label content including information to indicate a useful life of the medicinal substance stored in the source container based on the time established by the usage component. A printer is also included to print a label indicating the useful life of the medicinal substance in response to subsequent scanning of the label content.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Figure 1:
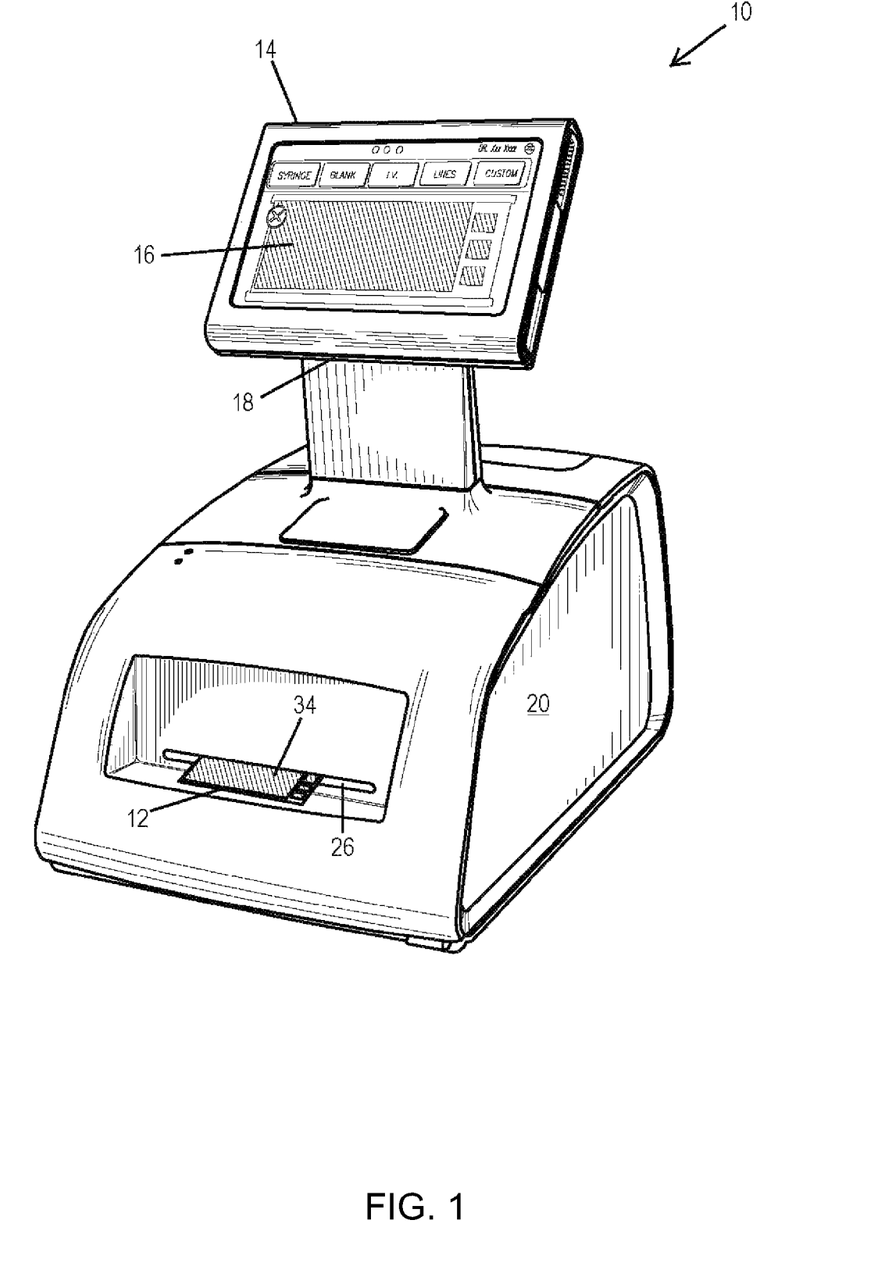
FIG. 1 shows an illustrative embodiment of a processor-controlled terminal including a scanner and a printer for producing a label for a medicinal substance.

FIG. 1 shows an illustrative embodiment of a terminal 10 including an integrated printer 26 for generating a label 12 to be used for labeling purposes in a healthcare, medical or life science application (referred to generally herein as a "medical application"). For embodiments where the labels 12 are to be used in a medical application, the printer 26 can optionally be configured to print a machine-readable code on the label 12 to facilitate record keeping with respect to the object on which the label 12 is to be applied. The machine-readable code printed by the printer 26 can streamline the entry of the information into a computer network when scanned. However, the description below also encompasses any conventional computer printer, including those that are computer peripherals to a conventional general-purpose computer. The label 12 may be used in any medical application such as identifying a medicinal substance in a syringe to be administered to a patient, labeling a medical device in a healthcare facility, labeling a medicinal substance to include expiration information, and labeling any other object encountered in the healthcare, medical or life science fields with any type of information, for example. However, for the sake of brevity, the generation of a label in a substantially-sterile condition for labeling a medicinal substance such as a medication in a syringe to be administered to a patient is described in the examples below.

As shown in FIG. 1, the computer terminal 10 may also include a touch-screen display 14 that displays information relating to the identification of a medicinal substance, an expiration date of the medicinal substance, and information regarding a patient. In other embodiments, the computer terminal 10 may not include a touch screen, but a conventional computer monitor, and other input peripherals such as a keyboard and mouse for example. The touch screen or other suitable display 14 may display a virtual label 16 to be printed as the label 12, and may display soft keys that can be touched by a technician or any user to input data and commands into the computer terminal 10.

The computer terminal 10 also includes a cabinet 20 housing components that are operable to produce the label 12. The cabinet 20 may be configured to operate in a substantially-sterilized condition. The label 12 can also optionally be compliant with a medical labeling standard addressing the content, format, arrangement, any other aspect of labels 12 to be employed in the medical field, or any combination thereof. The cabinet 20 can also support the display 14 and the scanner 18 to form a self-contained, stand-alone unit or can optionally use displays and scanners that are not integrated into the cabinet 20.

A processor component 160 (FIGS. 2-4) is provided within the cabinet 20. The processor component 160 is provided to execute computer-executable instructions stored in a non-transitory computer readable memory 165 (FIG. 2) such as a hard disk drive, read-only memory ("ROM"), random access memory ("RAM"), optical disc, or any other suitable memory device. The computer-executable instructions, when executed by the processor component 160, result in the performance of the method of generating a label for a medicinal substance described in detail below. A bus system or other suitable computer architecture, optionally a wireless architecture involved in a short-range wireless protocol such as Bluetooth, facilitates communication between components such as the display 14, scanner 18, processor component 160, memory, printer 26, and other components.

The computer terminal 10 can be deployed at a healthcare facility such as within an operating room at a hospital or surgical center, or anywhere a substantially-sterile label 12 is desired to minimize the risk of infection to a living organism, for example. An operating room, treatment room, or other substantially-sterile environment such can optionally be provided within the healthcare facility, and the printer 26 disposed within, or immediately adjacent to such a substantially-sterile environment. According to such embodiments, the label 12 can optionally be generated as described in detail below within, or at least within a close proximity to the substantially-sterile environment, or elsewhere the same facility where the label 12 is to be used.

For the illustrative embodiment of the label 12 shown in FIG. 1, the label content is applied by the printer 26 on a content surface 34 of the label 12 that is exposed and viewable by observers when the label 12 is applied to a syringe or other container storing the medicinal substance. An adhesive surface (opposite the content surface 34) can also be provided to be applied against a syringe, other container or any other object to adhere the label 12 to such objects.

The label content can include any identifying or other desired information about the object to be labeled, and is printed on-demand by the computer printer 26 under the control of one or more users who are involved in labeling the medicinal substance or other object in the medical field, or their agents. By "on demand" it is meant that the label is caused to be generated by the aforementioned users at a moment when the label 12 is desired. That moment can be when the label 12 is to be used for labeling purposes, such as when the label 12 is desired to be placed on a syringe storing a medicinal substance or while the syringe is being prepared, for example, or as needed at any other time prior to use of the label in the sterile environment. According to an alternate embodiment, the label 12 can be printed at a time when the syringe or other container is being prepared with the medicinal substance to be labeled, or shortly before or after preparation of the syringe or other container with the medicinal substance to be labeled.

In addition to the machine-readable code that can be interrogated by a suitable reading device such as the scanner 18 to identify the labeled medicinal substance, human-readable characters can also optionally be printed on the label surface 34. For example, alpha-numeric characters spelling the name and concentration of the medicinal substance, information indicating an expiration of the medicinal substance, and any other desired information can be printed on the content surface 34 to be read by humans without the assistance of a computer reading device. The human-readable characters can offer redundancy or be used as a quick reference to readily identify the medicinal substance in the absence of the scanner 18 or other suitable reader.

Figure 2:
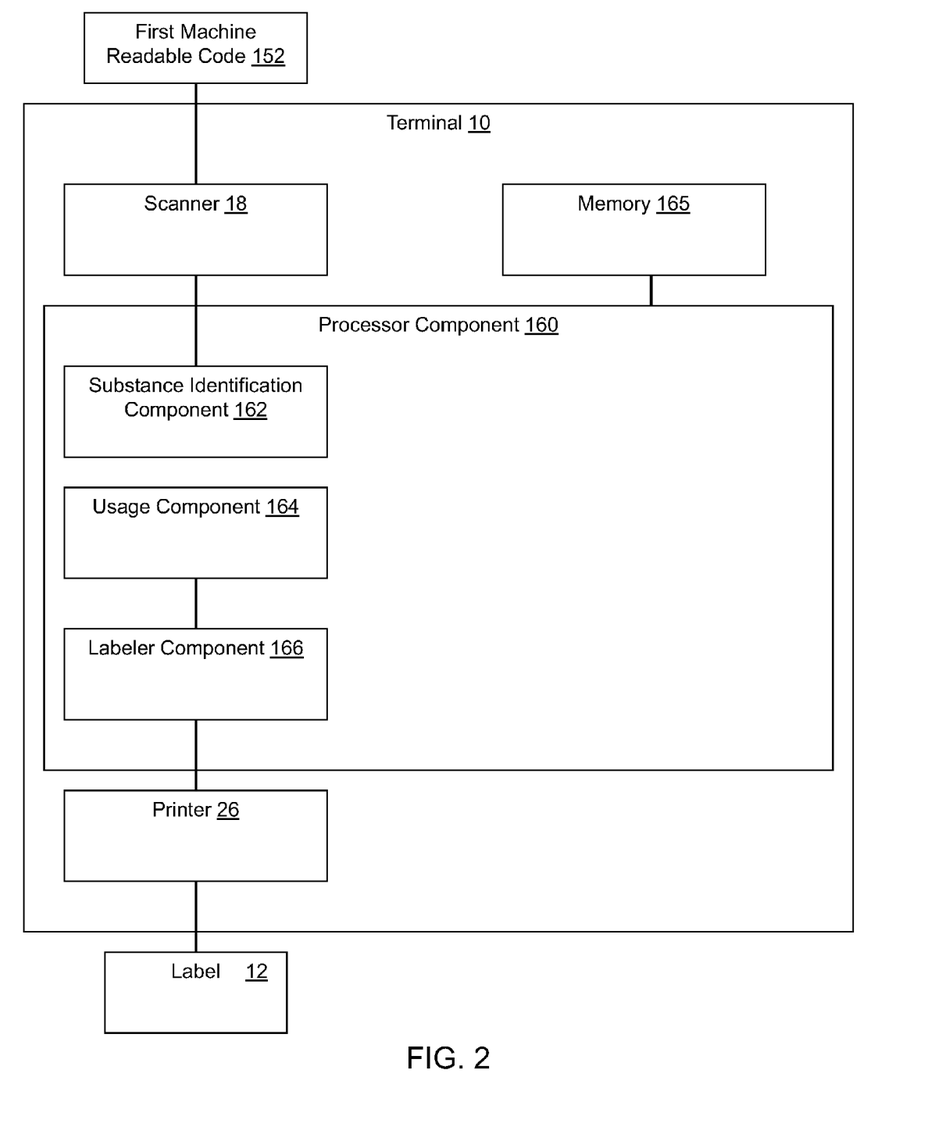
FIG. 2 shows a block diagram illustrating components of a processor-controlled terminal.

FIG. 2 includes a block diagram illustrating components of the terminal 10 shown in FIG. 1, and the interaction between those components and a machine-readable code 152 to generate the label 12 printed for labeling a medicinal substance.

The scanner 18 is operable to interrogate and convert the machine-readable code 152 associated with, and optionally adhered to, a source container storing the medicinal substance to be delivered to a patient into a signal that the processing component 160 can interpret to identify the medicinal substance.

The processor component 160 includes a substance identification component 162. The substance identification component 162 receives the signal transmitted from the scanner 18 in response to interrogating the machine-readable code 152. The signal can optionally be interpreted by the processor component 160 as a numerical or other suitable identifier that has been assigned to a medicinal substance in a medicinal substance database stored in the memory 165. Once the signal has been received by the processing component 160, the processing component 160 can query the medicinal substance database in an attempt to locate an entry therein that has also been assigned the identifier. The matching entry can be returned as a result of the query, thereby allowing the processing component 160 to determine the identity of the medicinal substance represented by the machine-readable code 152.

The first machine-readable code may be provided by a manufacturer of the medicinal substance. For example, the first machine-readable code may be affixed to a vial, alternately referred to herein as a primary package or unit dose, containing a drug to be administered to a patient. In another embodiment, the first machine-readable code may be associated with a secondary package that in which a plurality of the primary packages are packaged. For example, the primary package may be a vial containing the drug from which the medicinal substance is withdrawn using a syringe that will administer the medicinal substance to a patient, and a secondary package may be a box containing 12 vials, for example.

The processor component 160 also includes a usage component 164 that establishes a time at which the medicinal substance stored in the vial was initially accessed (i.e., when the vial was first breached). In one embodiment, the usage component 164 that establishes the time at which the medicinal substance stored in the source container was initially accessed is based on a time of said scanning of the first machine-readable code associated with the source container. For such an embodiment, the usage component can optionally use a system clock maintained by the terminal 10 as the reference time. The system clock can optionally be established and/or synchronized with other clocks of the healthcare facility over a communication network. In another embodiment, the usage component 164 uses a manually-entered time input by a user as the reference to establish the time of initial access.

The processor component 160 also includes a labeler component 166 that generates label content to be applied in machine-readable code, human-readable characters, or a combination thereof, on the content surface 34 of the label 12. The label content can include, in addition to at least one of the identification and concentration of the medicinal substance, information indicative of an end of a useful life of the medicinal substance stored in the vial from which the medicinal substance is withdrawn, in the syringe, or both. The information indicative of the end of the medicinal substance's useful life can include a preparation date and/or time at which a container is filled with the medicinal substance, an expiration date and/or time of the medicinal substance in the container, a duration of the useful life of the medicinal substance, any other information that can provide an indication when the medicinal substance in the container expires, or any combination thereof. The useful life can be determined based at least in part on the time established by the usage component 164.

The label content generated and assembled by the labeler component 166 is transmitted to the printer 26 for printing the label content onto the content surface 34 of the label 12 to indicate updated information that may have changed or been established since application of an existing label on container bearing the machine readable code 152. For instance, the information indicative of the useful life of the medicinal substance can be included on the label 12. In yet another embodiment, the printer 26 for printing the label 12 further includes label content to indicate the identity of the medicinal substance stored in the source container. The label 12 is provided with an optically-read machine-readable code, a radio frequency code stored by a radio-frequency identification (RFID) tag, or any other suitable machine-readable code that is readable by a computer-implemented reader.

Figure 3:
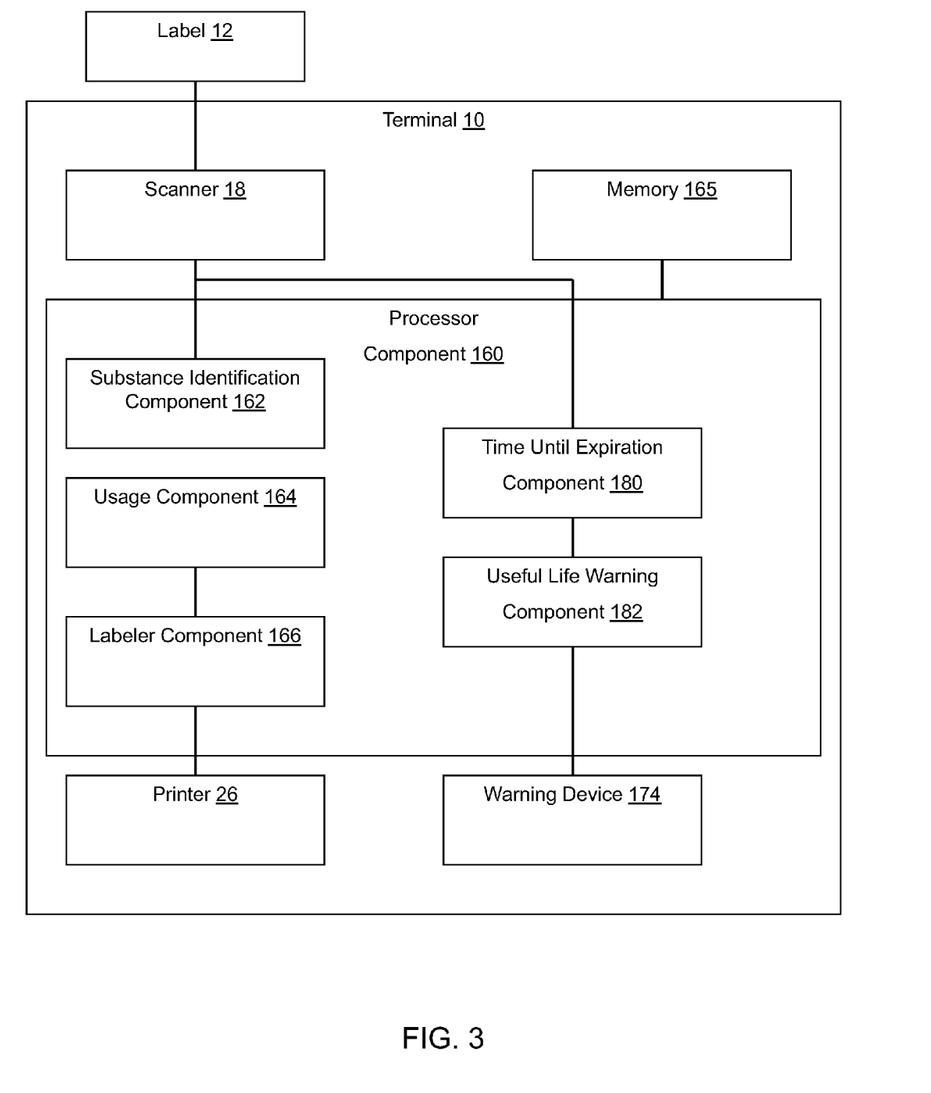
FIG. 3 shows a block diagram illustrating components of another aspect of the processor-controlled terminal shown in FIG. 2.

FIG. 3 shows yet another illustrative embodiment of the terminal 10 for labeling a medicinal substance. In this embodiment the scanner 26 scans the label 12 that was previously printed by the printer 26 of the terminal 10 or alternatively that was printed by another printer. The label 12 includes the label content, including the information indicative of the useful life of the medicinal substance.

The processor component 160 of the embodiment appearing in FIG. 3 includes a time until expiration component 180 to determine an amount of time before expiration of the medicinal substance, based on the information indicating a useful life of the medicinal substance and a time when the label 12 was scanned. For example, the time of scanning the label 12 may be a time when a clinician takes possession of the primary package to draw another syringe of the medicinal substance (i.e., draw a second syringe after the initial syringe was drawn and the label 12 created). The information indicating the useful life of the medicinal substance can be compared with the time when the primary package is accessed for drawing the second syringe to determine the amount of time left until the medicinal substance expires, or is otherwise deemed to be too old for continued use. Information indicative of the remaining useful life can be printed, in machine readable code and/or human readable characters, onto another label to be applied to the second syringe. Thus, the information indicative of the remaining useful life is included in the label content to be printed onto the label to be applied to the primary package when the primary package is initially breached (i.e., the seal on the primary package is initially broken, thereby exposed the medicinal substance therein to oxygen or an environment other than the inside of the primary package). Further, each time the primary package is subsequently reused to fill another syringe or other container, the information indicative of the remaining useful life can be extracted from the label 12 prepared and provided to the primary package as described herein, and included in label content to be printed on another label 12 printed for the syringe at a time when the another syringe is being used to fill the syringe. The information indicative of the remaining useful life to be printed on the label 12 to be applied to the syringe subsequently being filled can be different or the same as the information indicative of the useful life on the label applied to the primary package, and can optionally reflect the time that has passed since the primary package was initially breached.

As an example, consider a medicinal substance in a primary package that has a useful life after being initially accessed of 12 hours. If the primary package was initially breached at 11:00 am on a given date, the medicinal substance will be deemed to be expired as of 11:00 pm that same date.

If the primary package is accessed to supply the medicinal substance to a syringe at 10:00 pm that same day, the time until expiration component 180 can determine that 1 hour of useful life is left for the medicinal substance. Thus, a label 12 can be printed indicating that the medicinal substance in the second syringe is suitable to be administered within an hour of drawing the second syringe. At a time when the medicinal substance in the second syringe is to be administered, a clinician can use the scanner 18 to interrogate the label 12 on the second syringe to record the administration of the medicinal substance, and determine whether the end of the medicinal substance's useful life has been reached.

In another embodiment, the processor component 160 further includes a useful life warning component 182 to determine if the amount of time before expiration of the medicinal substance is less than a secondary useful life of the medicinal substance in a patient delivery device for delivering the medicinal substance to the patient, then to provide a useful life warning signal.

For example, propofol is a drug used by anesthesiologists in surgery that may have a 7 day life expectancy in a multi-use vial after the vial is initially accessed by a needle of a syringe to draw the drug from that vial. Thus, 7 days after the multi-use vial is initially breached it is recommended to discard any quantity of the drug remaining in the multi-use vial. However, the life expectancy of propofol in a syringe may only be 6 hours. Thus, propofol in a syringe is recommended to be administered to a patient no later than 6 hours after that syringe is filled with propofol. An anesthesiologist or other clinician preparing propofol for use during a surgical procedure may erroneously believe that the drug has a life expectancy of 6 hours in the syringe from the time the syringe is prepared. However, the drug in the multi-use vial may have a remaining life expectancy of only 1 hour because the vial containing the propofol was initially accessed 6 days and 23 hours earlier. In such a scenario, when the machine-readable code provided to the label 12 applied to the multi-use vial is scanned by the scanner 18, the useful life warning component 182 would issue a warning, informing the user that the expiration time of the syringe being prepared is less than the 6 hours that is the standard life expectancy of propofol in the syringe. The display 14 of the terminal 10 can optionally allow the user to input an override command, instructing the terminal 10 to print the label 12 for the syringe, and can optionally allow the user to input a discard command indicating that the remaining drug in the primary package has been disposed of and proceed to prepare a new label 12 to be applied to a new multi-use vial being opened by the user. In either or both instances, the terminal 10 can optionally record in the memory 160 an identifier of the user who input the override command and/or input the discard command for record-keeping purposes.

The display 14, an audio speaker, any other output device, or a combination thereof can be included as a warning device 174 that issues the warning to the user. The warning can be presented as an audio and/or a visual warning signal to a user based on the useful life warning signal.

In one embodiment, the time until expiration component 180 determines the information indicating a useful life of the medicinal substance, based on a time of said scanning of the label, the time that the medicinal substance was initially accessed, the identity of the medicinal substance, and an expiration time after initial access for the medicinal substance. Such information can optionally be stored in a formulary stored by the memory 160 provided to the terminal 10, can be accessed via a communication network, or a combination thereof. The label content further includes the time that the medicinal substance was initially accessed and the identity of the medicinal substance. The time until expiration component 180 or processor component 160 may include a database of expiration times after initial access for a plurality of medicinal substances and compare this list to the identity of the medicinal substance to determine the expiration time after initial access for the medicinal substance. The expiration time may be compared to the time of said scanning of the label, which may be the time of a subsequent access to the medicinal substance or a current time, to determine the information indicating a useful life of the medical substance.

The time until expiration component 180 can determine the information indicating a useful life of the medicinal substance, based on any information available to the terminal at a time of scanning a machine readable code with the scanner 18. For example, the time of scanning the label, the time that the medicinal substance was initially accessed, an amount of time until expiration after initial access of the medicinal substance, or any combination thereof can be factored into the information indicative of the remaining useful life.

Figure 4:
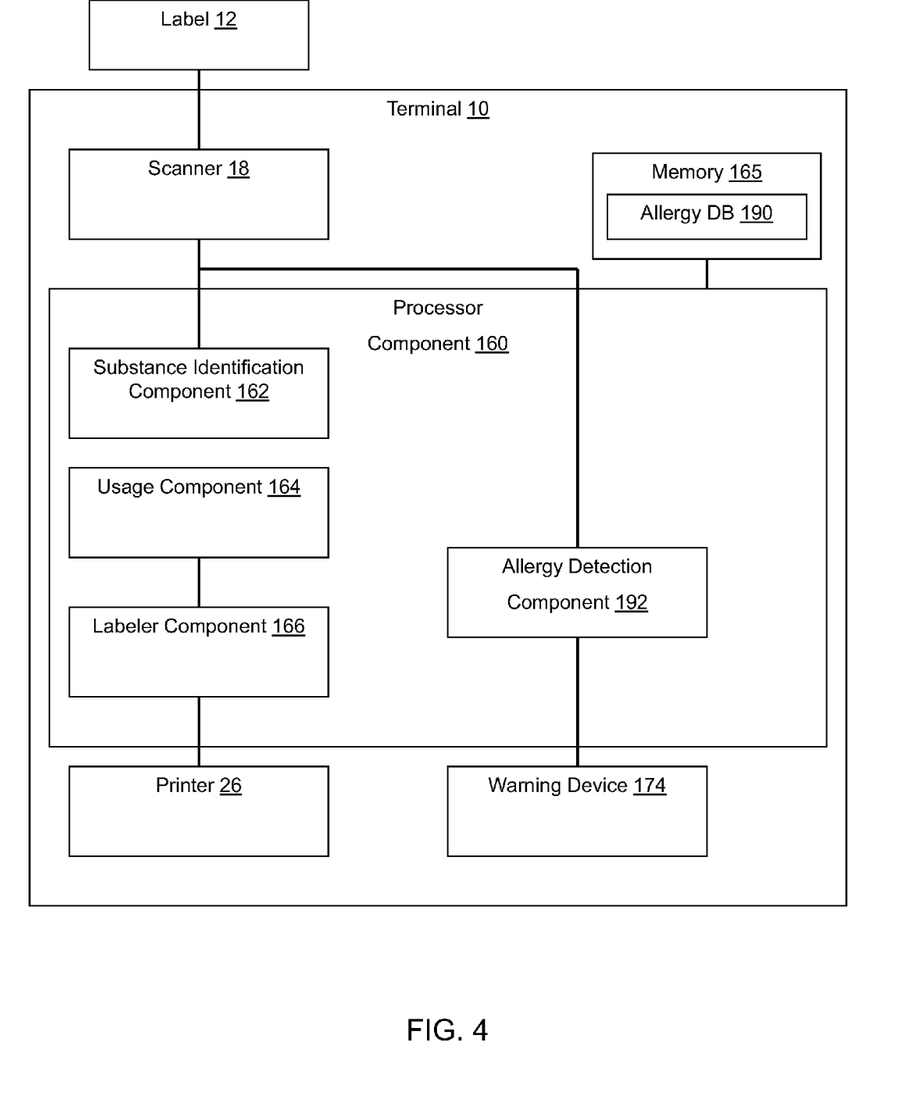
FIG. 4 shows a block diagram illustrating components of another aspect of the processor-controlled terminal shown in FIG. 2.

FIG. 4 shows yet another illustrative embodiment of the terminal 10 for labeling a medicinal substance. In this embodiment the scanner 18 scans the label 12 that was printed by the printer 26 of the terminal 10 or alternatively that was printed by another printer. The label 12 includes the information indicating the useful life of the medicinal substance. The label content also includes the identity of the medicinal substance.

The terminal 10 of the present embodiment also includes a patient allergy database 190 stored in the memory 165 that contains allergy information for the patient. During or before a surgical procedure, the identity of the patient can be entered into the terminal 10 and stored, at least temporarily, in the memory 165. The processor component 160 also includes an allergy warning component 192 that can conduct a query over a communication network in an attempt to retrieve allergy information for the patient whose identity was entered into the terminal 10. For example, the patient's allergy information can be retrieved from an electronic medical record ("EMR") for that patient stored in a network-connected storage device such as a medical record server. The allergy warning component 192 compares the patient's known allergies in the determines if the patient is allergic to the medicinal substance, based on the patient allergy database 190 to each drug that is identified by interrogating a machine readable code with the scanner 18 as described herein. If it is determined that an entry in the patient allergy database 190 matches one or more of the medicinal substances an allergy warning signal is transmitted by the allergy warning component 192.

The terminal 10 can also utilize the warning device 174 that provides an audio and/or visual warning signal to a user based on whether the allergy warning signal was provided by the allergy warning component 192.

In still other embodiments, the label 12 is configured to be affixed to a multi-use vial in locations including one or more of: the bottom of the multi-use vial, around a neck of the multi-use vial, in an open area of the multi-use vial not covered by the first machine-readable code, partially covering the first machine-readable code, and fully covering the first machine-readable code. According to other embodiments, the label 12 can be applied in a manner that does not substantially obfuscate substantive label content appearing on an existing label provided to the multi-use vial.

In other embodiments, computer-input peripherals such as a radio-frequency identification ("RFID") tag reader, or any other device that reads a machine-readable code such as a barcode or RFID code, respectively, or any other machine-readable code, with or without requiring contact between the computer terminal and the code, and optionally without requiring additional input from the user during entry of the code.

Figure 5:
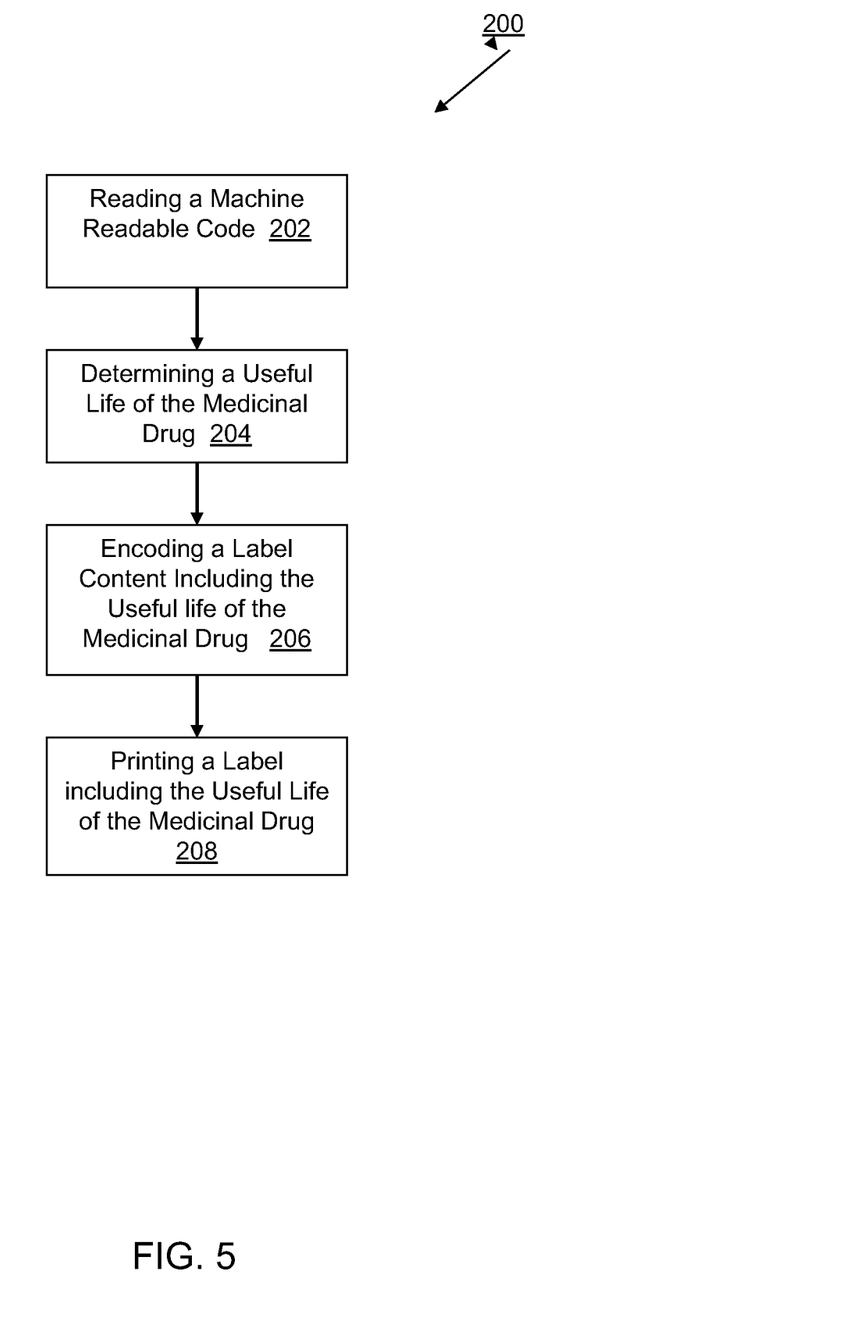
FIG. 5 shows an illustrative embodiment of a method for labeling a medicinal drug.

A method of labeling a medicinal drug 200 is illustrated schematically in FIG. 5. The method 200 includes reading a machine readable code 202 associated with a primary package or a secondary package. The primary package may be associated with a container for storing the medicinal drug. The container may be, for example, a vial containing a medication. The secondary package may include a plurality of primary packages. The machine readable code includes identification information of the medicinal drug. In another embodiment, the machine readable code may provide expiration information, expiration after initial use information, and/or expiration in a secondary container such as a syringe.

The method 200 also includes determining a useful life of the medicinal drug 204 based on a time at which the container for storing the medicinal drug was initially accessed.

Figure 6:
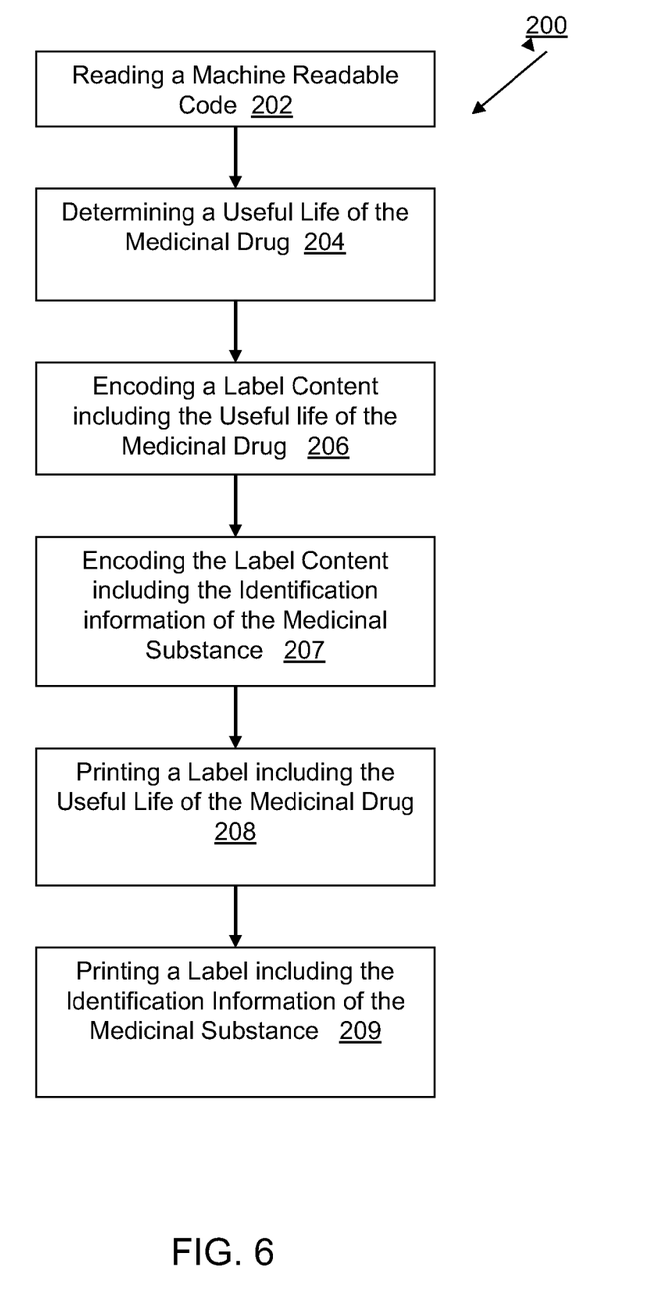
FIG. 6 shows another illustrative embodiment of a method for labeling a medicinal drug in FIG. 5.

The method of labeling the medicinal drug 200 also includes encoding a label content 206 including the useful life of the medicinal drug. In another embodiment, shown in FIG. 6, the method 200 further includes encoding the identification information of the medicinal drug 207, in addition to encoding the useful life of the drug 206.

The method of labeling the medicinal drug 200 also includes printing a label including the useful life of the medicinal drug 208 from the label content. In another embodiment, shown in FIG. 6, the method 200 further includes printing the label including the identification information of the medicinal drug 209 from the label content. This may be performed in addition to printing a label including the useful life of the medicinal drug 108. Both types of information may be printed on the same label or separate labels. In yet another embodiment, method 200 further includes, printing of the label including the useful life of the medicinal drug 208 in response to said reading of the machine readable code 202.

Figure 7:
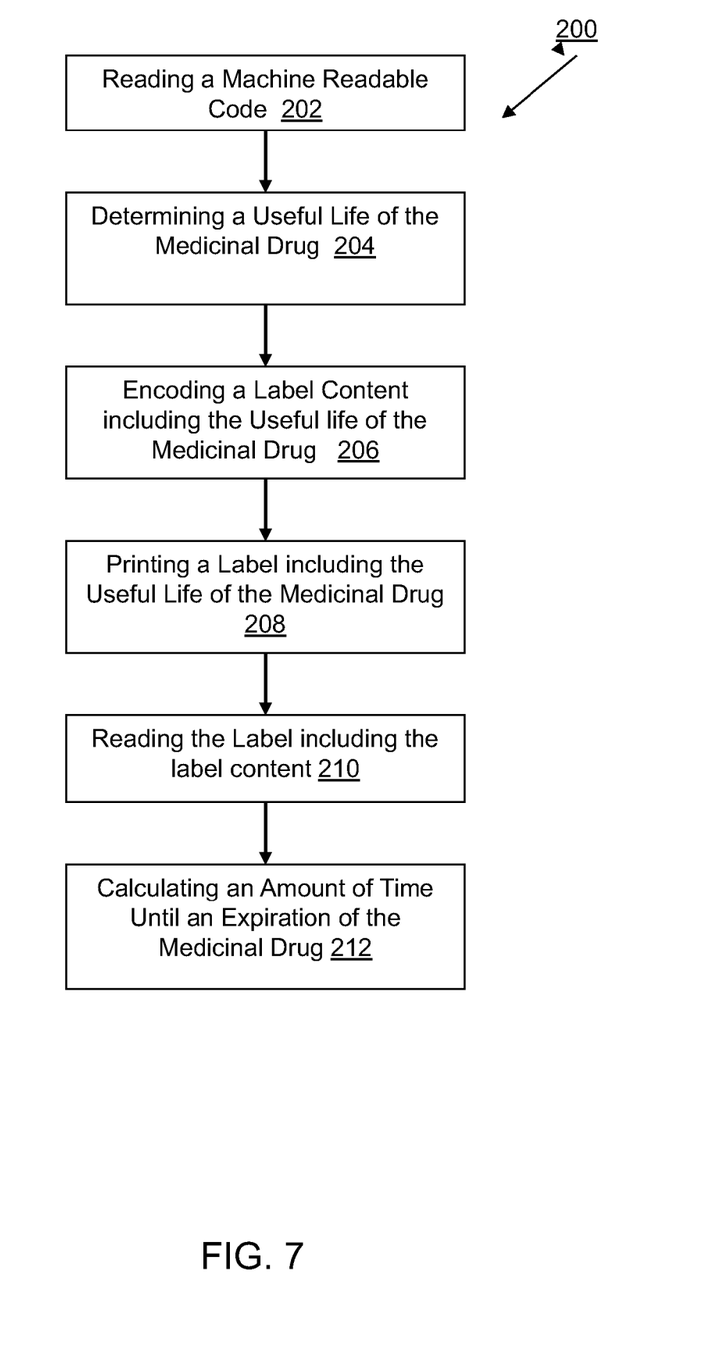
FIG. 7 shows an illustrative embodiment of a method for labeling a medicinal drug in FIG. 5.

In another embodiment, shown in FIG. 7, the method of labeling a medicinal drug 200 further includes reading the label including the label content 210. In still another embodiment, also shown in FIG. 7, the method 200 further includes, calculating an amount of time until an expiration of the medicinal drug 212 based on the useful life of the medicinal drug.

Figure 8:
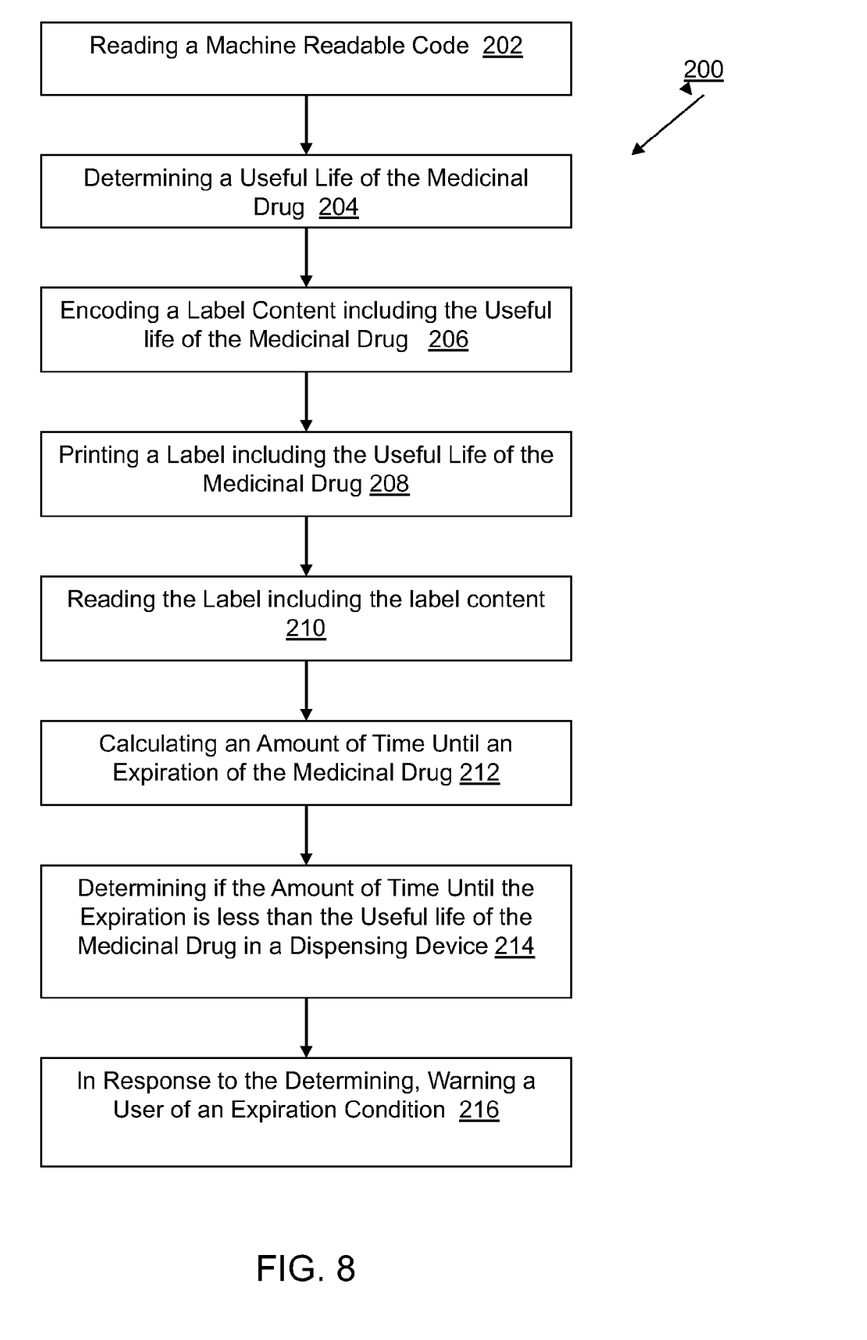
FIG. 8 shows an illustrative embodiment of a method for labeling a medicinal drug in FIG. 5.

In yet another embodiment, shown in FIG. 8, the method of labeling a medicinal drug 200 further includes determining if the amount of time until the expiration is less than the useful life of the medicinal drug in a dispensing device 214 used to dispense the medicinal drug to a patient. In yet another embodiment, also show in FIG. 8, the method 200 further includes, in response to the determining (in 214), warning a user of an expiration condition 216 via an audio alert and/or a visual alert. For example, if it is determined that the amount of time until expiration, based on the initial use, is 4 hours, and the life of the medicinal substance in a syringe is 6 hours, the user would be warned of the expiration condition 216.

Figure 9:
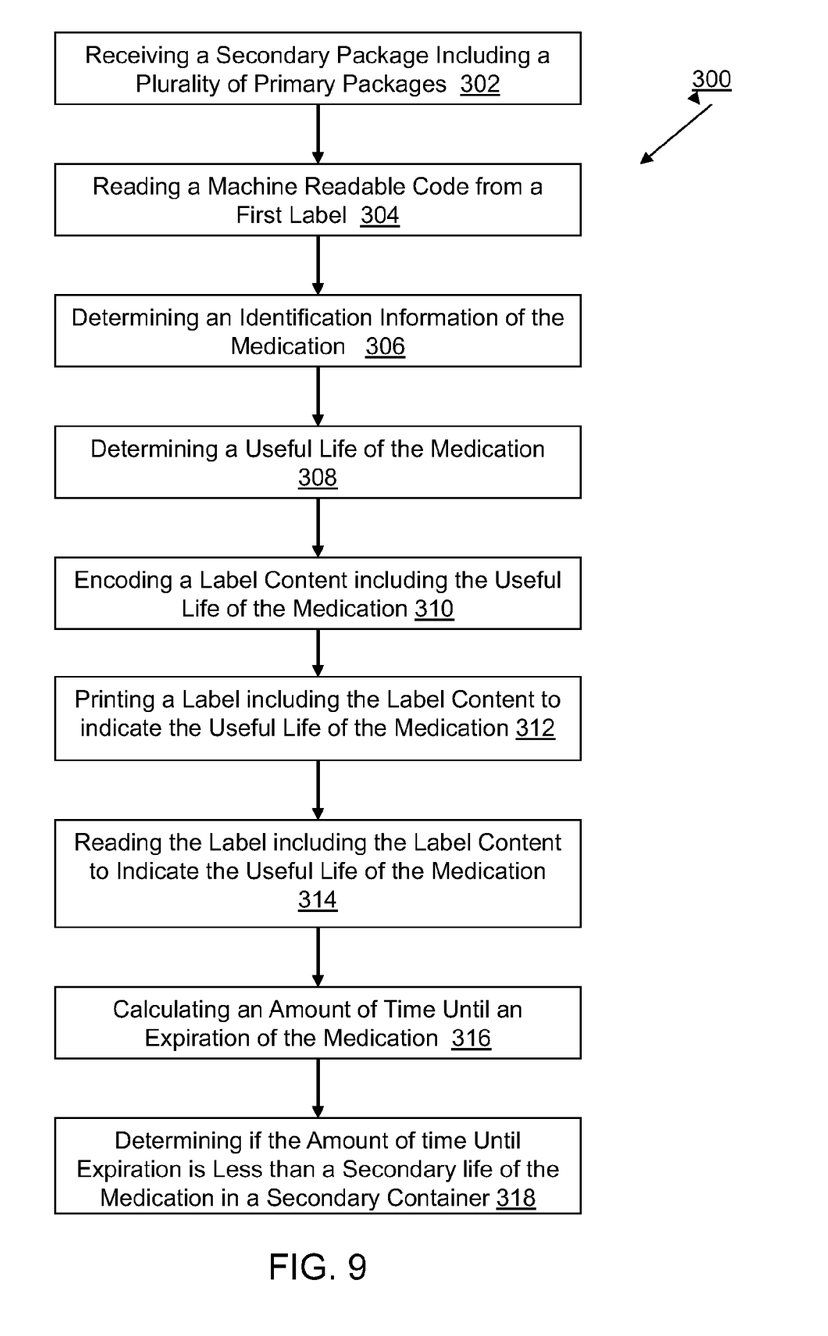
FIG. 9 shows an illustrative embodiment of method of labeling a medication in a hospital.

A method of labeling a medicinal drug 300 is illustrated schematically in FIG. 9. The method 300 includes, receiving a secondary package including a plurality of primary packages 302. At least one of the plurality of primary packages contains the medication. For example, the primary package may be a vial containing a drug or a source container containing a medicinal substance.

The method 300 also includes reading a machine readable code from a first label 304 associated with the secondary package or the at least one of the plurality of primary packages. In one example, the user may scan the secondary package containing multiple primary packages that contain the medication at the time the medication is initially accessed. The method 300 also includes, determining an identification information of the medication 306. The determining 306 may be based in part on the machine readable code that was read in 304.

The method 300 further includes, determining a useful life of the medication 308 based on a time at which the container for storing the medication was initially accessed. The time of initial accessing of the container may be the same time or substantially the same time as the reading of the machine readable code from the first label 304.

The method 300 also includes encoding a label content comprising the useful life of the medication 310. Method 300 also includes printing a label comprising the label content to indicate the useful life of the medication 312. Method 300 further includes reading the label comprising the label content indicating the useful life of the medication 314. Method 300 still further includes calculating an amount of time until an expiration of the medication 316 based on a time of said reading the label and the useful life of the medication.

The method 300 also includes determining if the amount of time until expiration is less than a secondary life of the medication in a secondary container 318. In response to said determining 318, warning a user via an audio alert and/or a visual alert.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus for labeling a medicinal substance comprising:
    a scanner that scans a first machine-readable code associated with a source container storing the medicinal substance to be delivered to a patient;
    a processor component comprising:
        a substance identification component that determines, based at least in part on said scanning of the first machine-readable code, an identity of the medicinal substance stored in the source container,
        a usage component that establishes a time at which the medicinal substance stored in the source container was initially accessed, and
        a labeler component that generates label content comprising information indicating a useful life of the medicinal substance stored in the source container in a machine readable format, based at least in part on the time established by the usage component; and
            a printer for printing a label comprising the label content to indicate the useful life of the medicinal substance in response to subsequent scanning of the label content.

2. The apparatus for labeling a medicinal substance of claim 1,
    wherein the usage component establishes the time at which the medicinal substance stored in the source container was initially accessed based on a time of said scanning of the first machine-readable code associated with the source container.

3. The apparatus for labeling a medicinal substance of claim 1,
  wherein said labeler component generates the label content further comprising the information indicating the identity of the medicinal substance stored in the source container, and
  said printer prints the label content to indicate the identity of the medicinal substance stored in the source container.

4. The apparatus for labeling a medicinal substance of claim 3,
  wherein the identity of the medicinal substance associated with the label is provided by one or more of:
    (a) the substance identification component that determines the identity of the medicinal substance stored in the source container,
    (b) a user input via a user interface,
    (c) the scanner that further scans a second machine-readable code of a second source container that is associated with the label and the source container, wherein the second source container is associated with the medicinal substance stored in the source container, and
    (d) the scanner that further scans a third machine-readable code of a secondary package that is associated with the source container.

5. The apparatus for labeling a medicinal substance of claim 1,
  wherein the first machine-readable code is associated with one or more of:
    a primary package associated with the source container storing the medicinal substance, and
    a secondary package that comprises a plurality of primary packages.

6. The apparatus for labeling a medicinal substance of claim 1, wherein
  said scanner is operable to scan the label comprising the label content to obtain information indicating the useful life of the medicinal substance; and
  said processor component further comprises a time until expiration component to determine an amount of time before expiration of the medicinal substance, based on the information indicating a useful life of the medicinal substance and a time of said scanning of the label.

7. The apparatus for labeling a medicinal substance of claim 6, said processor component further comprising:
  a useful life warning component to determine if the amount of time before expiration of the medicinal substance is less than a secondary useful life of the medicinal substance in a patient delivery device for delivering the medicinal substance to the patient, then to provide an useful life warning signal; and
  a warning device to provide an audio, a visual, or an audio and a visual warning signal to a user based on the useful life warning signal.

8. The apparatus for labeling a medicinal substance of claim 7,
  wherein the time until expiration component determines the information indicating a useful life of the medicinal substance, based on one or more of:
    (a) a time of said scanning of the label, the time that the medicinal substance was initially accessed, the identity of the medicinal substance, and an expiration time after initial access for the medicinal substance,
      wherein the label content further comprises: the time that the medicinal substance was initially accessed and the identity of the medicinal substance;
    (b) the time of said scanning of the label, and a time of expiration due to initial usage based on the time at which the medicinal substance stored in the source container was initially accessed,
      wherein the label content further comprises: the time of expiration due to initial usage; and
    (c) the time of said scanning of the label, the time that the medicinal substance was initially accessed, and an amount of time until expiration after initial access of the medicinal substance,
      wherein the label content further comprises: the amount of time until expiration after initial access of the medicinal substance and the time that the medicinal substance was initially accessed.

9. The apparatus for labeling a medicinal substance of claim 6,
  wherein the label content further comprises the identity of the medicinal substance;
  said processor component further comprising:
    a patient allergy database comprising allergy information for the patient, and
    an allergy warning component that determines if the patient is allergic to the medicinal substance, based on the identity of the medicinal substance and the allergy information for the patient, then to provide an allergy warning signal; and
    a warning device to provide an audio, a visual, or an audio and a visual warning signal to a user based on the allergy warning signal.

10. The apparatus for labeling a medicinal substance of claim 6,
  wherein the first machine-readable code is provided by a manufacturer of the medicinal substance,
  wherein the label is configured to be affixed to a multi-use vial in locations including one or more of:
    the bottom of the multi-use vial,
    around a neck of the multi-use vial,
    in an open area of the multi-use vial not covered by the first machine-readable code,
    partially covering the first machine-readable code, and
    fully covering the first machine-readable code,
  wherein the label is generated in response to said scanning of the first machine-readable code,
  wherein the label is a second machine-readable code comprising, and
  wherein the time until expiration component to determine an amount of time before expiration of the medicinal substance is further based on a time of said scanning of the label by the scanner or a time of a subsequent scanning of the label.

11. The apparatus for labeling a medicinal substance of claim 1, further comprising:
  a user interface for inputting data to the labeler component to be included in the label content.

12. The apparatus for labeling a medicinal substance of claim 11,
  said processor component, in response to one or more of said scanning of the first machine-readable code and said scanning of the label content, informs a user via the user interface of the identity of the medicinal substance.

13. The apparatus for labeling a medicinal substance of claim 1,
  wherein the label is one or more of: an optically read machine readable code and a radio frequency code, and
  wherein the scanner is configured to scan the label content from the label as one or more of: an optically read machine readable code and a radio frequency code.

14. A method of labeling a medicinal drug, comprising:
reading a machine readable code associated with a primary package or a secondary package,
wherein the primary package is associated with a container for storing the medicinal drug,
wherein the secondary package comprises a plurality of primary packages, and
wherein the machine readable code comprises, at least, an identification information of the medicinal drug;
determining a useful life of the medicinal drug based on a time at which the container for storing the medicinal drug was initially accessed;
encoding a label content comprising: the useful life of the medicinal drug;
printing a label comprising: the label content comprising: the useful life of the medicinal drug.

15. The method labeling the medicinal drug of claim 14, further comprising:
reading the label comprising the label content; and
calculating an amount of time until an expiration of the medicinal drug based on the useful life of the medicinal drug.

16. The method of labeling the medicinal drug of claim 15, further comprising:
determining if the amount of time until the expiration is less than the useful life of the medicinal drug in a dispensing device used to dispense the medicinal drug to a patient; then
in response to said determining, warning a user of an expiration condition via an audio alert, a visual alert, or an audio and a visual alert.

17. The method of labeling the medicinal drug of claim 16, wherein the useful life of the medicinal drug based on the time at which the container for storing the medicinal drug was initially accessed comprises, at least, one or more of:
(a) the time at which the container for storing the medicinal drug was initially accessed and the identification information of the medicinal drug,
(b) a time of expiration due to initial access to the container for storing the medicinal drug, and
(c) the time at which the container for storing the medicinal drug was initially accessed and an amount of time until the expiration due to initial access to the container for storing the medicinal drug.

18. The method of labeling the medicinal drug of claim 17, said calculating the amount of time until the expiration of the medicinal drug is further based on an another access time at which the container for storing the medicinal drug is accessed after the medicinal drug was initially accessed.

19. The method of labeling the medicinal drug of claim 14,
said encoding a label content further comprising: the identification information of the medicinal drug; and
said printing a label comprising: the label content further comprising: the identification information of the medicinal drug,
wherein said printing is in response to said reading of the machine readable code.

20. A method of labeling a medication in a hospital, comprising:
reading a machine readable code from a first label associated with a secondary package or at least one of a plurality of primary packages containing the medication;
determining, based at least in part on the machine readable code, an identity of the medication;
determining a useful life of the medication based on a time at which the container for storing the medication was initially accessed;
encoding the identity of the medication and the useful life in a machine-readable form to be included in label content; and
printing a label comprising the label content to indicate the identity and the useful life of the medication.

21. The method of labeling the medication of claim 20, further comprising:
reading the label comprising the label content indicating the useful life of the medication;
calculating an amount of time until an expiration of the medication based on a time of said reading the label and the useful life of the medication;
determining if an amount of time until an expected expiration of the medication in a delivery package is less than a remaining life of the medication labeled with the label; and
in response to determining that the amount of time until the expected expiration is later than the expiration of the medication, issuing a warning to a user via an audio alert, a visual alert, or an audio and a visual alert.

* * * * *